(12) United States Patent
Jessee et al.

(10) Patent No.: US 6,451,579 B1
(45) Date of Patent: Sep. 17, 2002

(54) REGULATED EXPRESSION OF RECOMBINANT PROTEINS USING RNA VIRUSES

(75) Inventors: Joel A. Jessee, Mount Airy; Valentina C. Ciccarone, Gaithersburg, both of MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/361,740

(22) Filed: Jul. 28, 1999

Related U.S. Application Data

(60) Provisional application No. 60/094,476, filed on Jul. 29, 1998.

(51) Int. Cl.$^7$ .............................. C12N 7/00; C12N 9/12
(52) U.S. Cl. .................... 435/235.1; 435/440; 435/455; 435/6; 435/320.1; 435/69.1; 435/15; 424/945; 514/44; 530/350; 530/435; 530/194
(58) Field of Search .................... 435/440, 194, 435/455, 69.1, 6, 15, 320.1; 514/44; 424/99.5; 530/350

(56) References Cited

U.S. PATENT DOCUMENTS

| | | | |
|---|---|---|---|
| 5,091,309 A | 2/1992 | Schlesinger et al. | 435/69.1 |
| 5,217,879 A | 6/1993 | Huang et al. | 435/69.1 |
| 5,532,154 A | 7/1996 | Brown | 435/235.1 |
| 5,578,473 A | 11/1996 | Palese et al. | 435/172.3 |

(List continued on next page.)

FOREIGN PATENT DOCUMENTS

| | | |
|---|---|---|
| EP | 0 716 148 A2 | 6/1996 |
| WO | WO 94/17813 | 8/1994 |
| WO | WO 96/17072 | 6/1996 |

(List continued on next page.)

OTHER PUBLICATIONS

Downes, T.E.H., et al., "The relative nutritive value of irradiated spray–dried blood powder and heat–sterilized blood meal as measured in combination with whey protein," *S. Afr. J. Anim. Sci.* 17:55–58, Pretoria Bureau Of Scientific Publications Of The Foundation For Education (1987).

Olivo, P.D. et al., "A Cell Line That Expresses a Reporter Gene in Response to Infection by Sindbis Virus: A Prototype for Detection of Positive Strand RNA Viruses," *Virology* 198:381–384, Academic Press, Inc. (1994).

Altman–Hamamdzic, S. et al., "Expression of β–galactosidase in mouse brain: utilization of a novel nonreplicative Sindbis virus vector as a neuronal gene delivery system." *Gene Therapy* 4:815–822 (Aug. 1997).

Artelt, P. et al., "Vectors for efficient expression in mammalian fibroblastoid, myeloid and lymphoid cells via transfection or infection," *Gene* 68:213–219 (1988).

Artuc, M. et al., "Differential promoter activity in benign and malignant human cells of skin origin," *Exp. Dermatol.* 4:317–321 (1995).

Barton, D. J. et al., "Demonstration In Vitro of Temperature–Sensitive Elongation of RNA in Sindbis Virus Mutant ts6," *J. Virol.* 62:3597–3602 (1988).

Bechler, K., "Influence of Capping and Polyadenylation on mRNA Expression and on Antisense RNA Mediated Inhibition of Gene Expression," *Biochem. Biophys. Res. Comm* 241:193–199 (Dec. 1997).

Berglund, P. et al., "Alphaviruses as vectors for gene delivery," *TIBTECH* 14:130–134 (Apr. 1996).

Bohl, D. et al., "Long–term control of erythropoietin secretion by doxycycline in mice transplanted with engineered primary myoblasts," *Nature Med.* 3:299–305 (Mar. 1997).

Bredenbeek, P. J. and C. M. Rice, "Animal RNA virus expression systems," *Seminars in Virol.* 3:297–310 (1992).

Bredenbeek, P. J. et al., "Sindbis Virus Expression Vectors: Packaging of RNA Replicons by Using Defective Helper RNAs," *J. Virol.* 67:6439–6446 (1993).

Burge, B.W. and E. R. Pfefferkorn, "Isolation and Characterization of Conditional–lethal Mutants of Sindbis Virus," *Virol.* 30:204–213 (1966).

Burge, B. W. and E. R. Pfefferkorn, "Complementation Between Temperature–sensitive Mutants of Sindbis Virus," *Virol.* 30:214–223 (1966).

Chapman, K. B. and J. W. Szostak, "Isolation of a ribozyme with 5'–5' ligase activity," *Chem. & Biol.* 2:325–333 (1995).

Crameri, A. et al., "Improved Green Fluorescent Protein by Molecular Evolution Using DNA Shuffling," *Nature Biotech.* 14:315–319 (Mar. 1996).

Davis, N. L. et al., "*In Vitro* Synthesis of Infectious Venezuelen Equine Encephalitis Virus RNA from a cDNA Clone: Analysis of a Viable Deletion Mutant," *Virol.* 171:189–204 (1989).

De Groot, R. J. et al., "Sindbis virus RNA polymerase is degraded by the N–end rule pathway," *Proc. Natl. Acad. Sci. USA* 88:8967–8971 (1991).

Doedens, J. R. et al., "Inhibition of Endoplasmic Reticulum–to–Golgi Traffic by Poliovirus Protein 3A: Genetic and Ultrastructural Analysis," *J. Virol.* 71:9054–9064 (Dec. 1997).

(List continued on next page.)

*Primary Examiner*—Rebecca E. Prouty
*Assistant Examiner*—Richard G. Hutson
(74) *Attorney, Agent, or Firm*—Sterne, Kessler, Goldstein & Fox P.L.L.C.

(57) ABSTRACT

The present invention describes cells and constructs for a regulated viral (e.g. alphavirus) expression system, where gene expression is controlled by controlling expression of replicases or nonstructural proteins and/or controlling the amount of such proteins introduced in a cell, which in turn regulates RNA replication and subsequently gene expression. Particularly, this system takes advantage of the high level expression of the alphavirus systems for recombinant protein production and allows for large scale applications without biosafety concerns.

9 Claims, 2 Drawing Sheets

U.S. PATENT DOCUMENTS

| | | | |
|---|---|---|---|
| 5,580,859 A | 12/1996 | Felgner et al. | 514/44 |
| 5,705,163 A | 1/1998 | Pastan et al. | 424/260.1 |
| 5,756,046 A | 5/1998 | Winks et al. | 422/32 |
| 5,756,349 A | 5/1998 | Lin | 435/325 |
| 5,789,245 A | 8/1998 | Dubensky, Jr. et al. | 435/320.1 |
| 5,792,462 A | 8/1998 | Johnston et al. | 424/199.1 |
| 5,814,482 A | 9/1998 | Dubensky et al. | 435/69.3 |
| 5,843,723 A | 12/1998 | Dubensky et al. | 435/69.3 |

FOREIGN PATENT DOCUMENTS

| | | |
|---|---|---|
| WO | WO 97/38087 | 10/1997 |
| WO | WO 98/36779 | 8/1998 |
| WO | WO 99/50432 | 10/1999 |

OTHER PUBLICATIONS

Dryga, S. A. et al., "Identification of Mutations in a Sindbis Virus Variant Able to Establish Persistent Infection in BHK Cells: The Importance of a Mutation in the nsP2 Gene," *Virol.* 228:74–83 (Feb. 1997).

Dubensky, Jr., T. W. et al., "Sindbis Virus DNA–Based Expression Vectors: Utility for In Vitro and In Vivo Gene Transfer," *J. Virol.* 70:508–519 (Jan. 1996).

Dubuisson, J. et al., "Formation and Intracellular Localization of Hepatitis C Virus Envelope Glycoprotein Complexes Expressed by Recombinant Vaccinia and Sindbis Viruses," *J. Virol.* 68:6147–6160 (1994).

Frolov, I. et al., "Alphavirus–based expression vectors: Strategies and applications," *Proc. Natl. Acad. Sci. USA* 93:11371–11377 (Oct. 1996).

Früh, K. et al., "Displacement of housekeeping proteasome subunits by MHC–encoded LMPs: a newly discovered mechanism for modualting the multicatalytic proteinase complex, " *EMBO J.* 13:3236–3244 (1994).

Furth, P. A. et al., "Temporal control of gene expression in transgenic mice by a tetracycline–responsive promoter," *Proc. Natl. Acad. Sci. USA* 91:9302–9306 (1994).

Gossen, M. and H. Bujard, "Tight control of gene expression in mammalian cells by tetracycline–responsive promoters," *Proc. Natl. Acad. Sci. USA* 89:5547–5551 (1992).

Hahn, C. S. et al., "Infectious Sindbis virus transient expression vectors for studying antigen processing and presentation," *Proc. Natl. Acad. Sci. USA* 89:2679–2683 (1992).

Hakimi, J. and P. H. Atkinson, "Glycosylation of Intracellular Sindbis Virus Glycoproteins," *Biochem.* 21:2140–2145 (1982).

Hariharan, M. J. et al., "DNA Immunization against Herpes Simplex Virus: Enhanced Efficacy Using a Sindbis Virus –Based Vector," *J. Virol.* 72:950–958 (Feb. 1998).

Henninghausen, L. et al., "Conditional Gene Expression in Secretory Tissues and Skin of Transgenic Mice Using the MMTV–LTR and the Tetracycline Responsive System," *J. Cell. Biochem.* 59:463–472 (1995).

Herweijer, H. et al., "A Plasmid–Based Self–Amplifying Sindbis Virus Vector," *Human Gene Ther.* 6:1161–1167 (1995).

Hoffmann, A. et al., "A novel tetracycline–dependent expression vector with low basal expression and potent regulatory properties in various mammalian cell lines," *Nucl. Acids. Res* 25:1078–1079 (Mar. 1997).

Howe, J. R. et al., "The Responsiveness of a Tetracycline –sensitive Expression System Differs in Different Cell Lines," *J. Biol. Chem.* 270:14168–14174 (1995).

Huang, H. V., "Sindbis virus vectors for expression in animal cells," *Curr. Opin. Biotech.* 7:531–535 (Oct. 1996).

Jeng, S.–Y. et al., "Characterization and Partial Purification of Bovine α–Lactalbumin and β–Casein Produced in Milk of Transgenic Mice," *J. Dairy Sci.* 80:3167–3175 (Dec. 1997).

Johanning, F. W. et al., "A sindbis virus mRNA polynucleotide vector achieves prolonged and high level heterologous gene expression in vivo," *Nucl. Acids Res.* 23:1495–1501 (1995).

Kawamata, H. et al., "Induction of TSC–22 by treatment with a new anti–cancer drug, vesnarinone, in a human salivary gland cancer cell," *Brit. J. Cancer* 77:71–78 (Jan. 1998).

Keränen, S. and L. Kääriäinen, "Functional Defects of RNA–Negative Temperature–Sensitive Mutants of Sindbis and Semliki Forest Viruses," *J. Virol.* 32:19–29 (1979).

Kerr, D. E. et al., "The bladder as a bioreactor: Urothelium production and secretion of growth hormone into urine," *Nature Biotech.* 16:75–79 (Jan. 1998).

Kistner, A. et al., "Doxycycline–mediated quantitative and tissue–specific control of gene expression in transgenic mice,"*Proc. Natl. Acad. Sci. USA* 93:10933–10938 (Oct. 1996).

Lavrovsky, Y. et al., "Therapeutic Potential and Mechanism of Action of Oligonucleotides and Ribozymes," *Biochem. Mol. Med* 61:11–22 (Oct. 1997).

Leake, C. J. et al., "Cytopathic Effect and Plaque Formation by Arboviruses in a Continuous Cell Line (XTC–2) from the Toad *Xenopus laevis,*" *J. gen. Virol.* 35:335–339 (1977).

Lee, K. H. et al., "Two–Dimensional Electrophoresis of Proteins as a Tool in the Metabolic Engineering of Cell Cycle Regulation,"*Biotech. Bioengin.* 50:336–340 (May 1996).

Lee, A. H. et al., "Comparison of Various Expression Plasmids for the Induction of Immune Response by DNA Immunization," *Mol. Cells* 7:495–501 (Aug. 1997).

Lemm, J. A. et al., "Mutation Which Alter the Level or Structure of nsP4 Can Affect the Efficiency of Sindbis Virus Replication in a Host–Dependent Manner," *J. Virol.* 64:3001–3011 (1990).

Lemm, J. A. and C. M. Rice, "Assembly of Functional Sindbis Virus RNA Replication Complexes: Requirement for Coexpression of P123 and P34," *J. Virol.* 67:1905–1915 (1993).

Liljeström, P. And H. Garoff, "A New Generation of Animal Cell Expression Vectors Based on the Semliki Forest Virus Replicon," *Bio/Technology* 9:1356–1361 (1991).

Liljeström, P., "Alphavirus expression systems," *Curr. Opin. Biotech.* 5:495–500 (1994).

Limonta, J. et al., "Production of active anti–CD6 mouse/human chimeric antibodies in the milk of transgenic mice," *Immunotech.* 1:107–113 (1995).

Lundstrom, K., "Alphaviruses as expression vectors," *Curr. Opin. Biotech.* 8:578–582 (Oct. 1997).

Mangelsdorf, D. J., "The Nuclear Receptor Superfamily: The Second Decade," *Cell* 83:835–839 (1995).

Máthé, E. et al., "The *Tomaj* mutant alleles of α*Tubulin67C* reveal a requirement for the encoded maternal specific tubulin isoform in the sperm aster, the cleavage spindle apparatus and neurogenesis during embryonic development in *Drosophila*," *J. Cell Sci.* 111:887–896 (Apr. 1998).

Meade, H. and C. Ziomek, "Urine as a substitute for milk?" *Nature Biotech* 16:21–22 (Jan. 1998).

Miki, T., "Heterogeneity of Sindbis Virus Glycoprotein $E_1$ and its Modification by Host Cell Transformation," *J. gen. Virol.* 65:343–354 (1984).

Minch, S. L. et al., "Tissue Plasminogen Activator Coexpressed in Chinese Hamster Ovary Cells with α(2,6)-Sialyltransferase Contains NeuAcα(2,6)Galβ(1,4)Glc–N–AcR Linkages," *Biotechnol. Prog.* 11:348–351 (1995).

Olkkonen, V. M. et al., "Expression of Exogenous Proteins in Mammalian Cells with the Semliki Forest Virus Vector," *Meth. Cell Biol.* 43:43–53 (1994).

Palese, P. et al., "Negative–strand RNA viruses: Genetic engineering and applications," *Proc. Natl. Acaed. Sci. USA* 93:11354–11358 (Oct. 1996).

Patterson, B. et al., "Cold–sensitive Mutants G680V and G691C of *Dictyostelium* Myosin II Confer Dramatically Different Biochemical Defects," *J. Biol. Chem.* 272:27612–27617 (Oct. 1997).

Paul, N. L. et al., "Expression of HIV–1 Envelope Glycoproteins by Semliki Forest Virus Vectors," *AIDS Res. and Hum. Retrovir.* 9:963–970 (1993).

Peng, L. et al., "Construction of Recombinant Adeno–Associated Virus Vector Containing the Rat Preproinsulin II Gene," *J. Surg. Res.* 69:193–198 (Apr. 1997).

Piper, R. C. et al., "Recombinant Sindbis Virus as an Expression System for Cell Biology," *Meth. Cell Biol.* 43:55–78 (1994).

Prodromou, C. and L. H. Pearl, "Recursive PCR: a novel technique for total gene synthesis," *Protein Engin.* 5:827–829 (1992).

Qing, K. et al., "Adeno–Associated Virus Type 2–Mediated Transfer of Ecotropic Retrovirus Receptor cDNA Allows Ecotropic Retroviral Transduction of Established and Primary Human Cells," *J. Virol.* 71:5663–5667 (Jul. 1997).

Renner, W. A. et al., "Recombinant Cyclin E Expression Activates Proliferation and Obviates Surface Attachment of Chinese Hamster Ovary (CHO) Cells in Protein–Free Medium," *Biotech. Bioeng.* 47:476–482 (1995).

Saez, E. et al., "Inducible gene expression in mammalian cells and transgenic mice," *Curr. Opin. Biotech.* 8:608–616 (Oct. 1997).

Schlesinger, M. J. and S. Schlesinger, "Formation and Assembly of Alphavirus Glycoproteins," in *The Togaviridae and Flaviviridae*, Plenum Press, New York, NY, pp. 121–148 (1986).

Schlesinger, S., "Alphaviruses—vectors for the expression of heterologous genes," *TIBTECH* 11:18–22 (1993).

Shockett, P. et al., "A modified tetracycline–regulated system provides autoregulatory, inducible gene expression in cultured cells and transgenic mice," *Proc. Natl. Sci. USA* 92:6522–6526 (1995).

Shockett, P. E. and D. G. Schatz, "Diverse strategies for tetracycline–regulated inducible gene expression," *Proc. Natl. Acad. Sci. USA* 93:5173–5176 (May 1996).

Schwer, B. et al., "Effects of deletion mutations in the yeast Ces1 protein on cell growth and morphology and on high copy suppression of mutations in mRNA capping enzyme and translation initiation factor 4A," *Nucl. Acids Res.* 26:803–809 (Feb. 1998).

Smith, S. M. et al., "Efficient Expression by an Alphavirus Replicon of a Functional Ribozyme Targeted to Human Immunodeficiency Virus Type 1," *J. Virol.* 71:9713–9721 (Dec. 1997).

Stanley, P., "Glycosylation engineering," *Glycobiology* 2:99–107 (1992).

Strauss, E. G. and J. H. Strauss, "Mutants of Alphaviruses: Genetics and Physiology," in *The Togaviruses*, Schlesinger, R. W., ed., Academic Press, New York, NY, pp. 393–426 (1980).

Strauss, J. H. and E. G. Strauss, "The Alphaviruses: Gene Expression, Replication and Evolution," *Microbiol. Rev.* 58:491–562 (1994).

Urakami, S. et al., "Overexpression of Members of the AP–1 Transcriptional Factor Family from an Early Stage of Renal Carcinogenesis and Inhibition of Cell Growth by AP–1 Gene Antisense Oligonucleotides in the *Tsc2* Gene Mutant (Eker) Rat Model," *biochem. and Biophys. Res. Comm.* 241:24–30 (Dec. 1997).

Wang, Y. et al., "A regulatory system for use in gene transfer," *Proc. Natl. Acad. USA* 91:8180–8184 (1994).

Wang, Y. et al., "Ligand–inducible and liver–specific target gene expression in transgenic mice," *Nature Biotech.* 15:239–243 (Mar. 1997).

Watson, E. et al., "Structure determination of the intact major sialylated oligosaccharide chains of recombinant human erythropoietin expressed in Chinese hamster ovary cells," *Glycobiology* 4:227–237 (1994).

Weiss, B. et al., "Establishment and Maintenance of Persistent Infection by Sindbis Virus in BHK Cells," *J. Virol.* 33:463–474 (1980).

Wimmel, A. et al., "Inducible acceleration of $G_1$ progression through tetracyclic–regulated expression of human cyclin E," *Oncogene* 9:995–997 (1994).

Wu, A. M. "In vivo veritas: Live phage display panning," *Nature Biotech.* 14:429–431 (Apr. 1996).

Xie, Y. et al., "A ribozyme–mediated, gene "knockdown" strategy for the identification of gene function in zebrafish," *Proc. Natl. Acad. Sci. USA* 94:13777–13781 (Dec. 1997).

Xiong, C. et al., "Sindbis Virus: An Efficient, Broad Host Range Vector for Gene Expression in Animal Cells," *Science* 243:1188–1191 (1988).

Yu, H. et al., "Inducible Human Immunodeficiency Virus Type 1 Packaging Cell Lines," *J. Virol.* 70:4530–4537 (Jul. 1996).

Zang, M. et al., "Production of Recombinant Proteins in Chinese Hamster Ovary Cells Using a Protein–Free Cell Culture Medium," *Biotech.* 13:389–392 (1995).

Invitrogen Manual, "Sindbis Expression System, Version C," from internet web page http://www.invitrogen.com/manuels.html, Catalog No. K750–01 (1996).

Dé, I. et al., "Sindbis Virus RNA–Negative Mutants That Fail to Convert Minus–Strand to Plus–Strand Synthesis: Role of the nsP2 Protein," *J. Virol.* 70:2706–2719 (1996).

DiCiommo, D. P. and R. Bremner, "Rapid, High Level Protein Production Using DNA–based Semliki Forest Virus Vectors," *J. Biol. Chem.* 273:18060–18066 (Jul. 1998).

Shirako, Y. and J.,H. Strauss, "Regulation of Sindbis Virus RNA Replication: Uncleaved P123 and nsP4 Function in Minus–Strand RNA Synthesis, whereas Cleaved Products from P123 Are Required for Efficient Plus–Strand RNA Synthesis," *J. Virol.* 68:1874–1885 (1994).

Suopanki, J. et al., "Regulation of alphavirus 26s mRNA transcription by replicase component nsP2," *J. Gen. Virol.* 79:309–319 (Feb. 1998).

Younker, D.R. and S.G. Sawicki, "Negative Strand RNA Synthesis by Temperature–Sensitive Mutants of Mouse Hepatitis Virus," *Coronaviruses and Arteriviruses*, Enjanes et al., eds., Plenum Press, New York, pp. 221–226 (Jul. 1998).

Boshart, M. et al., "A Very Strong Enhancer Is Located Upstream of an Immediate Early Gene of Human Cytomegalovirus," *Cell* 41:521–530 (1985).

Ciccarone, V. et al., "pSFV1 Eukaryotic Expression Vector: A Novel Protein Expression System," *Focus* 15:103–105 (1993).

Frese, M. et al., "Inhibition of Bunyaviruses, Phleboviruses, and Hantaviruses by Human MxA Protein," *J. Virology* 70:915–923 (1996).

Grakoui, A. et al., "A cis–Acting Mutation in the Sindbis Virus Junction Region Which Affects Subgenomic RNA Synthesis," *J. Virology* 63:5216–5227 (1989).

Kuhn, R.J. et al., "Mutagenesis of the 3' Nontranslated Region of Sindbis Virus RNA," *J. Virology* 64: 1465–1476 (1990).

Landis, H. et al., "Human MxA Protein Confers Resistance to Semliki Forest Virus amd Inhibits the Amplification of a Semliki Forest Virus–Based Replicon in the Absence of Viral Structural Proteins," *J.Virology* 72:1516–1522 (Feb. 1998).

Levis, R. et al., "Promoter for Sindbis Virus RNA–Dependent Subgenomic RNA Transcription," *J. Virology* 64:1726–1733 (1990).

Lundstrom, K. et al., "Effect of single point mutations of the human tachykinin $NK_1$ receptor on antogonist affinity," *Eur. J. Pharmacol.* 337:73–81 (Oct. 1997).

Meier, E. et al., "Activity of Rat Mx Proteins against a Rhabdovirus," *J. Virology* 64:6263–6269 (1990).

No, D. et al., "Ecdysone–inducible gene expression in mammalian cells and transgenic mice," *Proc. Natl. Acad. Sci. USA* 93:3346–3351 (1996).

Pavlovic, J. et al., "Resistance to Influenza Virus and Vesicular Stomatitis Virus Conferred by Expression of Human MxA Protein," *J. Virology* 64:3370–3375 (1990).

Scallan, M.F. et al., "bcl–1 Acts Early To Restrict Semliki Forest Virus Replication and Delays Virus–Induced Programmed Cell Death," *J. Virology* 71:1583–1590 (Feb. 1997).

Schneider–Schaulies, S. et al., "Cell Type–Specific MxA –Mediated Inhibition of Measles Virus Transcription in Human Brain Cells," *J. Virology* 68:6910–6917 (1994).

Schnorr, J.–J. et al., "MxA–Dependent Inhibition of Measles Virus Glycoprotein Synthesis in a Stably Transferred Human Monocytic Cell Line," *J. Virology* 67:4760–4768 (1993).

Staeheli, P., "Interferon–Induced Proteins and the Antiviral State," *Adv. Virus Res.* 38:147–200 (1990).

Zhao, H. et al., "Inhibition of Human Parainfluenza Virus–3 Replication by Interferon and Human MxA," *Virology* 220:330–338 (1996).

Wengler, G., "Chapter 16. Effects of Alphaviruse on Host Cell Macromolecular Synthesis," in *The Togaviruses. Biology Structure. Replication*, R.W. Schlesinger, ed., Academic Press, New York, NY, pp. 459–472 (1990).

Agapov, E.V. et al., "Noncytopathic Sindbis virus RNA vectors for heterologous gene expression," *Proc. Natl. Acad. Sci. USA* 95:12989–12994 (Oct. 1998).

Polo, J. M. et al., "Stable alphavirus packaging cell lines for Sindbis virus–and Semliki Forest virus–derived vectors," *Proc. Natl. Acad. Sci. USA* 964598–4603, The National Academy of Sciences of the USA (Apr. 1999).

FIGURE 1

1. | promoter | nsp 1-4 | 3' SFV | An | Poly A signal

2. | promoter | nsp 4* | 3' SFV | An | Poly A signal

3. | promoter | nsp 1+2+4 | 3' SFV | An | Poly A signal

4. | promoter | 5' SFV | 26S promoter | MCS | 3' SFV | An | Poly A signal

5. | promoter | nsp 1-4 | 26S promoter | MCS | 3' SFV | An | Poly A signal

6. | promoter | nsp 4* | 26S promoter | MCS | 3' SFV | An | Poly A signal

7. | promoter | nsp 1+2+4 | 26S promoter | MCS | 3' SFV | An | Poly A signal

\* The nsp 4 protein will contain a properly spaced ATG and TAA sequence.

FIGURE 2

| 8. | promoter | 5' SFV | 26S promoter | gene | 26S promoter | antibiotic gene | | |

| 9. | promoter | 5' SFV | 26S promoter | gene | IRES | antibiotic gene | | |

| 10. | promoter | 5' SFV | 26S promoter | gene | 26S promoter | antibiotic gene | | |

| 11. | promoter | 5' SFV | 26S promoter | gene | IRES | antibiotic gene | | |

| 12. | antibiotic[r] | 5' SFV | 26S promoter | MCS | 3' SFV | An | Poly A signal |

| 13. | promoter 1 | MxA protein | promoter 2 | Ab[r] | Poly A signal |

REGULATED EXPRESSION OF RECOMBINANT PROTEINS USING RNA VIRUSES

CROSS REFERENCE TO RELATED APPLICATION

The present application claims the benefit of U.S. Provisional Application No. 60/094,476, filed on Jul. 29, 1998, the contents of which are entirely incorporated herein by reference.

BACKGROUND AND SUMMARY OF THE INVENTION

Alphaviruses are single-stranded RNA viruses with a spike protein envelope structure. Even though infection usually occurs via a receptor-mediated endocytosis, naked viral RNA can initiate infection when introduced into the cytoplasm of a wide variety of host cells, including vertebrate and invertebrate cells. The 5' two-thirds of the 12-kb viral RNA encodes the four viral nonstructural, or replicase proteins nsp 1, nsp 2, nsp 3 and nsp 4, required for RNA amplification in the infected cell. The remaining third of the viral RNA codes for the structural proteins, the viral capsid and spike proteins, which are translated from the subgenomic 26S RNA with its own 26S promoter. Once the positive-sense RNA genome of the alphavirus is in the cytoplasm, it serves as the template for synthesis of a complementary negative strand by the virus-encoded replicase. The negative strand serves as the template for additional genomic RNA. Viral RNA replication is extremely rapid resulting in packaging of high titer alphavirus stocks of up to $10^{10}$ units per milliliter.

Due to its high replication efficiency, the simplicity of the replication cycle, i.e. the ability of the virus to replicate without a DNA intermediate, and its wide host range, alphaviruses have been studied for their potential as virus-based expression vectors. Since the virus requires only the presence of the replicase to replicate, the region encoding the replicase and all sequences required in cis for replication and packaging are maintained and the region encoding the structural proteins can be replaced with a desired gene. This type of viral vector with a replication capability is termed a replicon. It is currently possible with the alphavirus expression systems to split the replicon into two distinct replicons (Liljestrom and Garoff (1991) *Bio/Technology* 9:1356–1361; Xiong et. al. (1989) *Science* 243:1188–1191). One replicon contains all the viral structural genes and a replication signal, and is known as a helper plasmid or RNA. The second replicon contains the nonstructural proteins coding sequences, a signal for packaging of the RNA replicon, an expression cassette for expression of foreign genes (under control of the 26S promoter), and is known as the expression replicon. When the two RNA replicons are transfected into cells, it is possible for the nonstructural proteins of the expression vector to replicate the helper RNA and express the structural proteins, thus allowing for specific packaging of the expression replicon. These viral particles can then be used to infect cells and express protein. The replication of these RNA replicons is very rapid and a single RNA molecule can replicate up to 100,000 copies or more in 4–6 hours (Wengler, G. (1980) In: *The Togaviruses*. R. W. Schlesinger (ed.), Academic Press, New York, pp. 459–472).

The alphavirus expression systems using Semliki forest virus (SFV) (Liljestrom and Garoff (1991) *Bio/Technology* 9:1356–1361) and Sindbis (Xiong et al. (1989) *Science* 243:1188–1191; Dubensky et al. (1996) *J. Virol.* 70:508–519) have been extensively used to express recombinant proteins transiently, either as a transient transfection system, or by using viral particles to infect cells (Lundstrom K. (1997) *Cur. Opin. Biotechnol.* 8:578–582; Ciccarone et al. (1994) *Focus* 15: 103–105; Liljestrom, P. (1994) *Curr. Opin. Biotechnol.* 5:495–500). These systems have several advantages over other expression systems in that: 1) expression levels are high, and 2) viral particles can be generated and used to infect a variety of cell types so that authentic, post-translationally modified proteins can be made (Lundstrom et al. (1997) *Eur. J. Pharmacol.* 337:73–81).

Due to the fact that SFV and Sindbis are human pathogens, there are disadvantages with the viral expression system because of biosafety issues and problems with scale up. Under current regulations, the use of >$10^9$ viral particles requires a higher level of containment than a Biosafety Level 2 (BL2) laboratory making large scale viral infection and production, and subsequently, large scale manufacturing of proteins, problematic. Additionally, the viral life cycle is lethal in that a viral infection will kill cells at 48–96 hours post-infection or transfection, regardless of whether the viral RNA is introduced as packaged viral particles or by transfection of RNA followed by replication and protein expression. Some approaches have been described to control the replication rate of alphavirus RNA such as the overexpression of the anti-apoptotic protooncogene bcl-2 (Scallan, M. F. et al. (1997) *J. Virol.* 71:1583–1590), but this strategy only temporarily slowed viral replication and host cell apoptosis.

Therefore, there is a need for a non-viral or viral based expression system in which one could control the replication rate of these replicons so that they are not lethal to the host cell and which would allow for large-scale applications. In this system, an alphavirus DNA vector is utilized.

Alphavirus DNA vectors have been developed for both SFV (Berglund P., Tubulekas I., Liljeström P., Alphavirus as vectors for gene delivery, *Trends Biotechnol* 1996, 14:130–134) and Sinbis (Johanning F. W., Conry R. M., LoBuglio A. F., Wright M., Sumerel L. A., Pike M. J., Curiel D. T., A Sinbis Virus mRNA polynucleotide vector achieves prolonged and high level heterologous gene expression in vivo, *Nucleic Acids Res* 1995, 23:1495–1501; Herweijer H., Latendresse J. S., Williams P., Zhang G., Danko I., Schlesinger S., Wolf J. A., A plasmid-based self-amplifying Sindbis virus vector, *Hum Gene Ther.* 1995, 6: 1161–1167). In these DNA-RNA layered vectors a eukaryotic promoter is introduced upstream of the alphavirus replicase genes. DNA is transcribed to RNA from a recombinant eukaryotic promoter in the nucleus and transported to the cytoplasm, where the viral replicase takes over in the same way as during normal replication of alphavirus RNA molecules. The levels of reporter gene expression is 10–200-fold higher in mouse muscle cells for alphavirus DNA vectors than with conventional DNA vectors (Johanning, et al., infra, Herweijer, et al., infra; Dubensky, T. W., Driver, D. A., Polo, J. M., Belli, B. A., Latham, E. M., Ibanez, C. E., Chada S., Brumm D., Banks T. A., Mento S. J., et al., Sinbis virus DNA-based expression vectors: utility for in vitro and in vivo gene transfer,*J. Virol.* 1996, 70: 508–519). Expression is transient in nature as seen in mouse quadriceps, where no expression is detected 16 days post-injection. Therefore, alphaviruses can be efficiently used as tools in gene therapy for safe short-term gene expression.

The present invention relates to RNA virus expression and particularly to an alphavirus expression system in which one can control viral RNA replication so that it is not lethal or not substantially lethal to the host cell, and is therefore amenable to large scale production of RNA and protein. However, any viral expression system which employs RNA self-replication as a mechanism for viral amplification and expression can be used according to the present invention, including alphaviruses (animal viruses) such as togaviruses, i.e. Sindbis, SFV, Eastern Equine Encephalitis Virus (EEEV) and Venezuelan Equine Encephalitis Virus (VEEV), and flaviviruses, i.e. yellow fever virus, tick borne encephalitis virus; as well as plant viruses such as tobamoviruses (tobacco mosaic virus family) and bromoviruses (brome mosaic virus family) and variants, derivatives or modifications thereof. Viral RNA replication can be regulated by the methods discussed below.

Therefore, it is one object of the present invention to provide a method for controlling replication of viral RNA wherein cells are engineered to contain nucleic acid molecules (for example incorporated into the genome or into one or more vectors within the cells) having one or more of the virus (e.g. alphavirus) non-structural protein genes under the control of an inducible promoter. An expression construct (which may be RNA or DNA) containing the gene of interest under the control of a promoter (preferably an alphavirus recognized promoter) and having a replication signal (preferably an alphavirus recognized replication signal) may be stably introduced into the cell (e.g. by well known transfection or transformation techniques) or introduced after the cells are grown to high mass. When using a DNA molecule, the expression construct (containing the gene of interest under control of a promoter and the replication signal) is preferably under control of one or more promoters (which may be inducible and/or constitutive). When the desired RNA or protein is needed, the replicase or nonstructural genes are expressed by activating the inducible promoter. The replicase in turn recognizes the promoter and activates replication of the expression construct and expression of the gene of interest, resulting in the production of the desired RNA or protein which can be harvested by standard methods. It is another object of the present invention to provide expression constructs and cells for use in the method described above for controlling expression of replicase and viral replication, and protein production.

It is another object of the present invention to provide a method for controlling the amount of replicase (preferably alphavirus replicase) and hence the amount of viral replication in a cell and to methods of controlling expression of a desired protein using this system. Such methods may comprise introducing or transfecting cells, transiently or stably, with one or more replicase proteins (or nonstructural proteins) and/or with one or more replicase genes under regulateable control. The desired gene(s) to be expressed may be contained in one or more vectors may be contained in the genome of the cell. The gene of interest is preferably under the control of an alphavirus recognized promoter such as the 26S promoter. Thus, replication and expression of the desired gene would not take place or not be produced at elevated levels until one or more replicase or nonstructural proteins and/or other nonstructural genes are introduced, and gene expression and cell viability can thus be controlled until appropriate cell growth has been achieved. Methods for the delivery of one or more replicase or nonstructural proteins (e.g. nsp 1–4 proteins) are described. Expression constructs and cells for use in a method for controlling viral replication in a cell by introducing the nonstructural proteins and/or genes (or combinations thereof) into a cell containing a gene encoding a desired protein are also described.

It is yet another object of the present invention to provide expression constructs and cells for use in a method for controlling viral replication and expression in a cell by introducing into the cell a factor or drug which inhibits viral RNA replication.

As will be understood, these methods, expression constructs and cells may be applied to any number of RNA viral systems by using appropriate replicase or nonstructural proteins/genes and genetic constructs.

Other preferred embodiments of the present invention will be apparent to one of ordinary skill in the art in view of the following drawings and description of the invention.

BRIEF DESCRIPTION OF THE DRAWINGS

FIG. 1 is a schematic representation of possible arrangements of the nonstructural proteins, the promoters, and 5' and 3' sequences. Promoter=inducible or constitutive promoter; nsp 1–4, SFV nonstructural proteins 1–4; 3' SFV, SFV termination signals; $A_n$, a stretch of >25 nucleotides of Adenylic acid; Poly A signal, polyadenylation signal; nsp 4*, only nonstructural protein 4 is used and will contain properly spaced start and stop codons for proper expression of the protein; nsp 1+2+4, nonstructural protein 1, 2, and 4 are included; 26S promoter, subgenomic promoter recognized by the SFV replicase; 5'SFV, SFV replication signal; MCS, multiple cloning site containing endonuclease restriction sites for ease of inserting the gene of interest.

FIG. 2 shows the possible arrangements of a construct with the gene of interest. Promoter: inducible or constitutive promoter; 5' SFV, SFV replication signal; 26 S promoter, subgenomic promoter recognized by SFV replicase; gene, gene of interest; internal ribosome entry sites (IRES), antibiotic gene, antibiotic resistance gene, or a selectable marker for selecting transformants.

DETAILED DESCRIPTION OF THE INVENTION

In the description that follows, a number of terms used in recombinant DNA technology are extensively utilized. In order to provide a clearer and consistent understanding of the specification and claims, including the scope to be given such terms, the following definitions are provided.

Replicon

Any genetic element, e.g. a plasmid, a chromosome, a virus, that behaves as an autonomous unit of polynucleotide replication within a cell; i.e., capable of replication under its own control.

Cloning Vector

A plasmid, cosmid or phage or other nucleic acid molecule (e.g. RNA or DNA) which is able to replicate autonomously in a host cell, and which is characterized by one or a small number of restriction endonuclease recognition sites at which such sequences may be cut in a determinable fashion without loss of an essential biological function of the vector, and into which nucleic acid may be spliced in order to bring about its replication and cloning. The cloning vector may further contain a marker suitable for use in the identification of cells transformed with the cloning vector.

Expression Vector

A vector similar to a cloning vector but which is capable of enhancing the expression of a gene which has been cloned into it, after transformation or transfection into a host. The cloned gene is usually placed under the control of (i.e., operably linked to) certain control sequences such as promoter sequences.

Recombinant Host

Any prokaryotic or eukaryotic organism, microorganism or bacteria which contains the vector or vectors, or contains the desired cloned genes in an expression vector, cloning vector of any nucleic acid molecule. The term "recombinant host" is also meant to include those host cells which have been genetically engineered to contain the desired vectors or genes on the host chromosome or genome.

Host

Any prokaryotic or eukaryotic organism, microorganism or bacteria that is the recipient of a replicable expression vector, cloning vector or any nucleic acid molecule. The molecule may contain, but is not limited to, a structural gene, a promoter and/or an origin of replication.

Gene

A nucleic acid sequence that contains information necessary for expression of a polypeptide or protein. It includes the promoter and the structural gene as well as other sequences involved in expression of the protein. When a gene is under the control of a 26S promoter, there will generally be some or no 5' untranslated region, an ATG at the start of the coding sequence and a stop codon. The gene of interest may also comprise additional sequences to create fusion proteins to facilitate protein purification, such as His tags, GST tags and the like.

Expression Construct

Any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription and translation of a gene into a gene product. In other embodiments, expression only includes transcription of the nucleic acid encoding the gene, which can be useful for making RNA for antisense gene therapy Promoter A nucleic acid sequence or transcription control element generally described as the 5' region of a gene and/or other sequence, located proximal to the start codon. At the promoter region, transcription of an adjacent gene(s) or sequence(s) is initiated.

Constitutive Promoter

A transcription control element which is continuously functional, i.e., cannot be induced nor repressed, and results in the continuous expression of a gene operably linked to it. Constitutive promoters include promoters for housekeeping genes, or genes which are continuously expressed in the cell. Examples of such promoters include human cytomegalovirus (CMV) immediate early gene promoter, the SV40 early promoter and the Rous sarcoma virus long terminal repeat.

Inducible Promoter

A transcriptional control element which can be regulated in response to specific signals. Table 1 lists several promoters which may be employed in the context of the present invention to regulate the expression of genes or sequences operably linked to such promoters.

TABLE 1

Promoters and Their Inducible Factors

| Element | Inducer |
|---|---|
| 1. MTII | Phorbol Ester (TPA), Heavy metals |
| 2. MMTV (mouse mammary tumor virus) | Glucocorticoids |
| 3. b-interferon | poly(rI)X, poly(rc) |
| 4. Adenovirus 5 E2 | E1a |
| 5. c-jun | Phorbol Ester(TPA), $H_2O_2$ |
| 6. Collagenase | Phorbol Ester(TPA) |
| 7. Stromelysin | Phorbol Ester(TPA), IL-1 |
| 8. SV-40 | Phorbol Ester(TPA) |

TABLE 1-continued

Promoters and Their Inducible Factors

| Element | Inducer |
|---|---|
| 9. Murine Mx Gene | Interferon, Newcastle Disease Virus |
| 10. GRP78 Gene | A23187 |
| 11. a-2-macroglobulin | IL-6 |
| 12. Vimentin | Serum |
| 13. HSP70 | E1a, SV-40 Large T Antigen |
| 14. Tumor Necrosis Factor | FMA |
| 15. Thyroid Stimulating Hormone | Thyroid Hormone |
| 16. Tetracycline regulated Promoter | Tetracycline |
| 17. Ecdysone inducible Promoter | Ecdysone, Muristerone, Ponasterone A |

Bicistronic Vector

A nucleic acid vector with an arrangement of promoter and two sequences resulting in RNA transcripts produced from the same start site, one encompassing a first sequence, and another transcript including the first sequence and the sequence 3' of the first sequence.

Polyadenylation Signal

A nucleic acid sequence which allows the addition of a sequence of polyadenylic acid to the 3' end of a RNA (preferably eukaryotic RNA) after its transcription. The nature or presence of the polyadenylation signal is not believed to be crucial to the successful practice of the invention, and any such sequence may be employed if its use is desired. The SV40 polyadenylation signal was used for convenience and known to function in the target cells of interest. Also contemplated as an element of an introduced nucleic acid is a termination signal which serves to minimize read through.

Marker

A nucleic acid sequence coding for a marker, usually cloned into a vector for use in the identification of cell transformed or transfected with the vector. A marker would result in an identifiable change to the transfected or transformed cell permitting easy identification of expression or delivery of nucleic acid in vitro or in vivo. Usually the inclusion of a drug selection marker aids in cloning and in the selection of transformants or transfectants. Alternatively, enzymes such as herpes simplex virus thymidine kinase (tk) (eukaryotic) or chloramphenicol acetyltransferase (CAT) (prokaryotic) may be employed. Immunologic markers also can be employed. Further examples of selectable markers are known to one of skill in the art.

Delivery of Nucleic Acid to Cells

Delivery of the desired nucleic acids to cells or host cells can be accomplished in vitro, as in laboratory procedures for transforming or transfecting cell lines, or in vivo, or ex vivo. Methods include calcium phosphate precipitation (Graham and Ven Der Eb (1973); Chen and Okayama, (1987); Rippe et al. (1990)), DEAE Dextran (Gopal, (1985)), electroporation (Tur-Kaspa et al. (1986); Porter et al., (1984)), direct microinjection (Harland and Weintraub, (1985)), DNA-loaded liposomes (Nicolau and Sene, (1982); Fraley et al. (1979)) and lipofectin-DNA or cationic lipid-DNA (Hawley-Nelson, et al., Lipofectamine (1993) *Focus*, 15: 73–78; Ciccarone, et al., DMRIE-C (1995) *Focus*, 17: 84–87) complexes, cell sonication (Felgner et al., (1987)), gene bombardment using high velocity microprojectiles (Yang et al., (1990)) and receptor-mediated transfection (Wu and Wu, (1987); Wu and Wu, (1988)). Some of these techniques may be successfully adapted for in vivo or ex vivo use. How the nucleic acid is delivered to a cell is dependent on the type of nucleic acid employed.

Stable Cell Line

Once the nucleic acid (e.g. RNA and/or DNA) has been delivered into the cell, the nucleic acid may be positioned and expressed at different sites. In certain embodiments, the nucleic acid may be stably integrated into the genome of the cell, producing a stable cell line. This integration may be in the cognate location and orientation via homologous recombination, or it may be integrated in a random non-specific location. The nucleic acid may be stably maintained in the cell as a separate, episomal segment. Such nucleic acid segments or "episomes" encode sequences sufficient to permit maintenance and replication independent of or in synchronization with the host cell cycle, wherein the cell the nucleic acid remains is dependent on the type of vector employed.

The present invention describes methods, vectors, cell lines, and agents for the regulated control of gene expression using an alphavirus replicon or other RNA viral systems.

In one embodiment, the present invention provides a method for the regulated control of alphavirus or other virus replicon and gene expression by controlling the amount of replicases or nonstructural proteins expressed by a cell line. As such, using the expression system of the present invention, one can produce a cell line containing the nucleic acid molecules capable of expressing one or more genes encoding nonstructural proteins (e.g. nsp 1–4), or some combination of these nonstructural proteins, under the control of an inducible and/or constitutive promoter. Preferably, at least one nonstructural protein gene is under control of an inducible promoter. This can be done, for example, by introducing a vector or vectors containing one or more of the nonstructural protein genes operably linked to a promoter (different combinations of constitutive and inducible promoters may be used but preferably at least one replicase or nonstructural protein gene is under control of an inducible promoter) into the desired cells. The vector can be any vector but is preferably a DNA vector. The one or more nonstructural protein genes may be integrated into the host genome or may be contained in one or more vectors or various combinations of such genes may be both integrated in the genome and contained in one or more vectors. For integration, a constitutive promoter controlling expression of a selectable marker (neo, hygro, puro, blasticidin) is preferred. For episomal or vector maintenance, a selectable marker (as above) and an origin of replication (EBNA, etc.) is required. The vector also preferably contains an *Escherichia coli* origin of replication and a selectable marker with a prokaryotic promoter for selection and maintenance in *Escherichia coli*, although other prokaryotic or eukaryotic origins and/or markers may be used depending on the need or host cell used. In another aspect of the invention, the gene of interest or expression construct may be contained by the same vector/genome having the one or more nonstructural protein genes.

The cells containing the one or more genes for the nonstructural proteins are allowed to multiply until the desired number of cells or cell mass is reached. The gene of interest to be expressed under the control of one or more transcriptional control elements or promoters preferably recognized by the nonstructural viral replicases, such as the 26S promoter for SFV, can be induced when the desired number of cells or cell mass has been reached thereby producing high levels of the desired protein. Preferably, the genes of interest are contained by one or more expression vectors which may be integrated into the host genome or maintained as one or more expression replicons (or combinations thereof). Following induction of replication, and gene expression, cells can be harvested to isolate the protein of interest.

For example, genes encoding some or all of the nonstructural proteins (or various combinations thereof) can be positioned under a constitutive or a regulated promoter. Preferably, at least one nonstructural protein gene is under control of a regulatable promoter. When nsp 4 is the only nonstructural protein gene used, the nsp 4 will contain a properly spaced translation initiation codon (ATG) and a translation termination codon (TAA). The promoter sequences used in the invention may be constitutive promoters such as cytomegalovirus (CMV) promoter (Boshart, M. et al. (1985) *Cell* 41:521–530) or an inducible promoter system such as the tetracycline-regulated promoter (Gossen, M. and Bujard, H. (1992) *PNAS USA* 89:5547–5551; Shockett, P. et al. (1995) *PNAS USA* 92:6522–6526) or the ecdysone inducible promoter (No, D. et al. (1996) *PNAS USA* 93:3346–3351). The nsp 1,2,3, and 4 are the nonstructural proteins of SFV and the 5' SFV signal contains the sequences necessary for replication (Levis R. et al. (1990) *J. Virol.* 64:1726; Grakoui, A. et al. (1989) *J. Virol.* 63:5216). The 3' end of the construct will include 3' SFV termination signals (Kuhn, R. J. et al. (1990) *J. Virol.* 64:1465), a stretch of 25 nucleotides of A, and the SV40 termination and polyadenylation signals.

The nonstructural proteins, the inducible promoter and the 5' and 3' sequences can be arranged in several ways as diagramed in FIG. 1.

Stable cell lines are generated with constructs 1–3 of FIG. 1 that express all or some of the SFV nonstructural proteins under control of either a constitutive promoter (i.e. CMV) or an inducible promoter (tetracycline-inducible minimal CMV, or ecdysone inducible-pIND). For ecdysone or muristerone inducible expression, the vectors are co-transfected with a vector encoding the ecdysone responsive element pVgRXR (No et al., 1996, supra). Stable transfection of any mammalian or insect cell line (e.g. CHO, BHK, Drosophila, Spodoptera cell lines) is achieved by either co-transfection with a second vector encoding a positive selectable marker (neo$^r$, blasticidin$^r$, hygro$^r$, puromycin$^r$) or by incorporating the selectable marker on the same vector. The selected clonal cell lines will then express the one or more of the nonstructural genes either constitutively (for CMV promoter) or upon induction by either a) removal of tetracycline from medium, or b) addition of the ecdysone analog, muristerone or ponasterone A to the cell medium.

These established cell lines can then be transiently or stably transfected with nucleic acid molecules (e.g. RNA or DNA, preferably vectors) encoding a gene of interest expressed under control of, for example, the SFV 26S promoter, and are thus capable of generating replicating RNA molecules using the nonstructural proteins of, for example, SFV or other alphaviruses. RNA replication is dependent on the SFV nonstructural protein 4 replicase, and may be achieved by the presence of the 5' SFV replication signal (as in construct 4 of FIG. 1). Thus, replication and expression of the SFV-encoded RNA would not take place or would not be produced at elevated levels until the cells are induced to express the replicase and/or other SFV nonstructural genes, and gene expression and cell viability can thus be controlled until appropriate cell growth has been achieved. Such control will allow maximum production of the protein of interest. In the case where the stable cell line encodes the nonstructural genes under a constitutive promoter, the expression construct or vector or any expression vector or replicon or nucleic acid molecule of interest containing the gene to be expressed is transiently transfected or transformed into large scale cultures and replication and expression begin directly after transfection or transformation. Where inducible regulation is used, such expression vectors or replicons may be introduced into the cell line at any time and protein expression may then be accomplished upon induction of expression of the one or more nonstructural proteins. Cells are harvested for protein isolation (typically 24–48 hours post-transfection).

This strategy can also be achieved by stable transfection of a single vector or construct, as in constructs 5–7 of FIG. 1, where both the gene of interest and one or more nonstructural genes are encoded on the same vector, and expression of the nonstructural genes is regulated by an inducible promoter. Stable cell lines that contain such vectors or constructs are scaled up to appropriate cell mass and induced to express nonstructural proteins, thus allowing expression of the gene of interest from for example the 26S promoter and replication of RNA.

In another embodiment, vectors encoding a gene of interest and antibiotic resistance gene (for example, puromycin$^r$, hygromycin$^r$ or blasticidin$^r$ for rapid selection), under control of SFV 26S promoter (as in construct 8 of FIG. 2), is transfected into a cell line that expresses the SFV nsp genes under control of an inducible promoter. The cells are placed under selective pressure by addition of the antibiotic, then grown to a high cell mass. At this point the cells are induced to express the nsp genes, which in turn drive RNA replication and overexpression.

Alternatively, a bicistronic vector can be created (as in vector 9 of FIG. 2) which expresses both the antibiotic resistance gene and gene of interest under control of a single 26S promoter. Thus any cell that expresses antibiotic resistance must also express the gene of interest. Similarly, this vector is transfected into a stable cell line which expresses the SFV nsp genes from an inducible promoter. After antibiotic selection, the promoter that drives expression of the replicase is induced, and cells are harvested for the protein of interest.

In yet another embodiment of the present invention is a method for controlling alphavirus or other virus replicon expression by initiating replication and protein expression in cells by introducing one or more nonstructural proteins (preferably one or more SFV nonstructural proteins) into the cells that contain the gene of interest under control of one or more promoters (e.g. 26S promoters). As will be appreciated, the amount of protein introduced may be used to regulate the level of expression of the gene of interest (i.e. introduction of more nonstructural proteins may be used to increase expression) and the amount of protein introduced can be optimized for the particular system used. The nonstructural proteins in any combination may be introduced into cells by methods known to a person with skill in the art. For example, proteins can be delivered to a cell using cationic lipids, such as lipofectamine or DMRIE-C (Sells, et al, (1995) *Biotechniques,* 19: 72–75). Alternatively, a fusion protein with a peptide or protein sequence which has a transport function can be used. For example, the HIV Tat protein or a peptide component of Tat (Mann and Frankel (1991) EMBO J. 10:1733–1739; Frankel et al. (1989) PNAS USA 86:7397–7401) and the Herpesvirus VP22 protein (Elliot, G. et al. (1997) Cell 88:223–233) and membrane translocating sequence (MTS) (Rojas, et al., (1998) *Nature Biotechnology,* 16: 370–375) have been shown to mediate the uptake into cells of a heterologous protein when the protein is synthesized as a fusion with the transport protein or peptide. As will be recognized, some nonstructural proteins may be introduced by these introduction methods while other proteins may be expressed by these introduction methods described above. Thus, various combinations of nonstructural protein expression and introduction of nonstructural proteins may be utilized in accordance with the invention.

For example, a stable cell line is constructed which contains the SFV nsp 1–3 genes under an inducible and/or constitutive promoters (if under the CMV promoter) (as in vectors 1–3 of FIG. 1) and, on the same or separate vector, the gene of interest is under control of the SFV 26S promoter (as in vectors 10 and 11 of FIG. 2). Expression of the nsp 1–3 genes is therefore constitutive or induced to drive expression. Once the desired cell population density is achieved, RNA replication and enhanced gene expression is achieved by introduction of the nsp 4 replicase protein into the cells. The protein can be introduced with cationic lipids or, more efficiently, as synthetic fusions with a peptide or protein that has a transport function and allows the fused protein to cross the cell and nuclear membranes (i.e. as Tat, MTS or VP22 fusion proteins).

Therefore, gene expression can be induced at moderate to high levels in the cell population, while retaining viability, by expression of the nsp 1–3 genes and subsequently activation of the 26S promoter. Once cell confluency is reached, replication can be induced by delivery of the nsp 4 replicase protein (at various amounts or concentrations) and cells can then be harvested for protein isolation (e.g. hours later).

Alternatively, the nsp 1–4 proteins can also be delivered to cells. In this case, cells are stably transfected with a vector that encodes the gene of interest under control of the SFV 26S promoter (as in vector 10, 11, or 12 of FIG. 2). Both gene expression and RNA replication are induced by delivery of nsp 1–4 proteins as a complex with cationic lipids or as fusion proteins.

In yet another embodiment of the present invention, a drug or agent which inhibits viral replication is introduced into a cell. Alphavirus or other virus RNA replication can be inhibited by proteins or drugs which have antiviral activity. Mx proteins, for example, which are GTPases induced by interferons (Staehli, P. (1990) *Adv. Virus Res.* 38:147–200) have been shown to inhibit the multiplication of negative-strand RNA viruses (Frese, M. et al. (1996) *J. Virol.* 70:915–923; Meier, E. et al. (1990) *J. Virol.* 64:6263–6269; Pavolvic, J. et al. (1990) *J. Virol.* 64: 3370–3375; Zhao, H. et al. (1996) *Virology* 220:330–338). The human MxA protein, specifically, was found to block the multiplication of influenza virus at the level of RNA synthesis or synthesis of viral glycoproteins (Schneider-Schaulies, S. et al. (1994) *J. Virol.* 68:6910–6917; Schnorr, J. et al. (1993) *J. Virol.* 67:4760–4768), and was also found to have antiviral activity to SFV by inhibiting RNA replication at the level of synthesis or function of the viral replicase (Landis, H. et al. (1998) *J. Virol.* 72: 1516–1522). The MxA protein can therefore be utilized to control replication of recombinant RNA virus (e.g. SFV) and therefore regulate gene expression.

For example, a stable cell line is constructed with human MxA protein under control of an inducible promoter (e.g. a tetracycline or muristerone-regulated promoter). The expression of the MxA protein is kept in the induced state until RNA replication is required. This stable cell line is then transfected with a vector such as construct 5 of FIG. 1 or a combination of constructs (e.g. construct 1 (FIG. 1) and construct 10 or 11 (FIG. 2)) to express the nsp genes and the gene of interest. RNA replication, however, will be inhibited or prevented by the expression of the MxA protein. When MxA induced expression is shut off either by addition of tetracycline or removal of muristerone from the medium, RNA replication and expression is allowed.

When the desired protein is expressed and produced by the transfected or transformed cell to the desired level, the protein can be collected either from the supernatant, if the protein is secreted, or by harvesting the cells and extracting the desired protein by methods known in the art, and specific for the desired protein.

The methods, cells and vectors of the present invention can be used to produce therapeutic compounds and/or to provide therapeutic compounds to specific cells, tissues, organs or organisms. Therapeutic compounds include protein, RNA, and DNA cloned into the vectors for providing a clinical effect. Proteins provided for therapeutic purposes would include antigens for the production of an immunogenic response against a pathogen, or a drug for treatment of a disease or disease symptoms. RNA could be provided for the production of a protein as described above, or alternatively, antisense RNA is provided such that translation of an undesired protein or factor is inhibited or reduced. DNA can be provided encoding a protein or RNA as described above, and further for a marker, or for expression of a gene operably linked to such DNA allowing a drug to effect the expression of a desired gene, or for integration into the host genome in order to disrupt a targeted gene.

Where clinical applications of the present invention are contemplated, it may be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct and/or cells of the invention, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic, and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hyroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The expression constructs and delivery vehicles of the present invention may include classic pharmaceutical preparations. Administration of therapeutic compositions according to the present invention will be via any common route so long as the target tissue or cell is available via that route. This includes oral, nasal, buccal, rectal, vaginal, or topical. Topical administration would be particularly advantageous for treatment of skin cancers, for example. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers, or other excipients.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact composition are adjusted according to well known parameters.

Additional formulations are suitable for oral administration. Oral formulations include such typical excipients as, for example, pharmaceutical grades of mannitol, lactose, starch, magnesium, stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray. An effective amount of the therapeutic agent is determined based on the intended goal. The term "unit dose" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic compositions also depend on the judgement of the practitioner and are peculiar to each individual.

All the materials and reagents required for expressing a desired gene using the present invention may be assembled together in a kit. This generally will comprise one or more of the following: selected cell lines which are capable of expressing or accepting the viral nonstructural proteins, and/or constructs to be used along with the cell line in which a gene or genes of interest can be inserted such that they may be expressed when introduced into the cell line. Also included may be various media or antibiotics for replication and selection of host cells, as well as drugs or agents suitable for inhibiting viral replication. Additionally, the kit may include transfection reagents, i.e. cationic lipid transfection reagents. Such kits may comprise distinct containers for each individual reagent or such reagents may be combined in containers in various combinations and concentrations.

When the components of the kit are provided in one or more liquid solutions, the liquid solution preferably is an aqueous solution, with a sterile aqueous solution being particularly preferred.

The components of the kit may also be provided in dried or lyophilized forms. When reagents or components are provided as a dried from, reconstitution generally is by the addition of a suitable solvent. It is envisioned that the solvent also may be provided in another container means.

The kits of the present invention also will typically include a means for containing the vials in close confinement for commercial sale such as, e.g. injection or blow-molded plastic containers into which the desired vials are retained.

The following examples are included to demonstrate preferred embodiments of the invention. It should be appreciated by those of skill in the art that the techniques disclosed in the examples represent techniques discovered by the inventors and thought to function well in the practice of the invention, and thus can be considered to constitute preferred, but non-limiting, modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1
Cloning of Non-structural Proteins under a Constitutive or a Regulated Promoter The promoter sequence is either a constitutive promoter such as cytomegalovirus (CMV) promoter (Boshart, M. et al. (1985) *Cell* 41:521–530) or an inducible promoter system such as the tetracycline-regulated promoter (Gossen, M. and Bujard, H. (1992) *PNAS USA* 89:5547–5551; Shockett, P. et al. (1995) *PNAS USA* 92:6522–6526) or the ecdysone inducible promoter (No, D. et al. (1996) *PNAS USA* 93:3346–3351). The nsp 1,2,3, and 4 are the non-structural proteins of SFV and the 5' SFV signal contains the sequences necessary for replication (Levis R. et al. (1990) *J. Virol.* 64:1726; Grakoui, A. et al. (1989) *J. Virol.* 63:5216). The 3' end of the construct will include 3' SFV termination signals (Kuhn, R. J. et al. (1990) *J. Virol.* 64:1465), a stretch of 25 nucleotides of A, and the SV40 termination and polyadenylation signals.

The nonstructural proteins, the inducible promoter and the necessary 5' and 3' sequences can be arranged in several ways as diagramed in FIG. 1.

Stable cell lines are generated with constructs 1–3 of FIG. 1 that express all or some of the SFV nonstructural proteins under control of either a constitutive promoter (e.g., CMV) or an inducible promoter (tetracycline-inducible minimal CMV, or ecdysone inducible-pIND). For ecdysone, ponasterone A or muristerone inducible expression, the vectors are co-transfected with a vector encoding the ecdysone responsive element pVgRXR (No et al., 1996, supra). Stable transfection of any mammalian or insect cell line (e.g. CHO, BHK, Drosophila, Spodoptera cell lines) is achieved by either co-transfection with a second vector encoding a positive selectable marker (neo$^r$, blasticidin$^r$, hygro$^r$, puromycin$^r$) or by incorporating the selectable marker on the same vector. The selected clonal cell lines will then express the SFV nonstructural genes and protein either constitutively (for CMV promoter) or upon induction by either a) removal of tetracycline from medium, or b) addition of the ecdysone analog, muristerone or ponasterone A to the cell medium.

These established cell lines can then be transiently or stably transfected with vectors encoding a gene of interest expressed under control of the SFV 26S promoter, and are thus capable of generating replicating RNA molecules using the nonstructural proteins of SFV or other alphavirus. RNA replication is dependent on the SFV nonstructural protein 4 replicase, and may be achieved by the presence of the 5' SFV replication signal (as in construct 4 of FIG. 1). Thus, replication and expression of the SFV-encoded RNA would not take place at high levels until the cells are induced to express the replicase and other SFV nonstructural genes, and gene expression and cell viability can thus be controlled until appropriate cell growth has been achieved. In the case where the stable cell line encodes the nonstructural genes under a constitutive promoter, the SFV expression vector is transiently transfected into large scale cultures and replication and expression begins directly after transfection. Cells are harvested for protein isolation 24–48 hours post-transfection. Alternatively, these stable cell lines can also be transfected with a truncated SFV replicon without the nsp such that the RNA molecule will not replicate until the stable cell is induced to replicate.

This strategy can also be achieved by stable transfection of a single vector, as in constructs 5–7 of FIG. 1, where both the gene of interest and nonstructural genes are encoded on the same vector, and expression of the nonstructural genes is regulated by an inducible promoter. Stable cell lines that contain this vector are scaled up to appropriate cell mass and induced to express nonstructural proteins, thus allowing expression of the gene of interest from the 26S promoter and replication of RNA.

Example 2
Expression Constructs with Selectable Marker under 26s Promoter and Bicistronic Vectors for Use with Stable Cell Line with nsp Genes Vectors encoding gene of interest and antibiotic resistance gene (blasticidin$^r$ for rapid selection), under control of SFV 26S promoter (as in construct 8 of FIG. 2), are transfected into a cell line that expresses the SFV nsp genes under control of an inducible promoter. The cells are placed under selective pressure by addition of the antibiotic, then grown to a high cell mass. At this point the cells are induced to express the nsp genes, which in turn drive RNA replication and overexpression.

Alternatively, a bicistronic vector can be created (as in vector 9 of FIG. 2) which expresses both the antibiotic resistance gene and gene of interest under control of a single 26S promoter. Thus any cell that expresses antibiotic resistance must also express the gene of interest. Similarly, this vector is transfected into a stable cell line which expresses the SFV nsp genes from an inducible promoter. After antibiotic selection, the promoter that drives expression of the replicase is induced, and cells are harvested for protein.

Example 3
Induction of SFV RNA Replication by Introduction of Replicase Protein into Cells A stable cell line is constructed which contains the SFV nsp 1–3 genes under an inducible or constitutive promoter (if under the CMV promoter) (as in vectors 1–3 of FIG. 1) and, on the same or separate vector, the gene of interest is under control of the SFV 26S promoter (as in vectors 10 and 11 of FIG. 2). Expression of the nsp 1–3 genes is therefore constitutive or induced to drive expression of the genes of interest. Once the desired cell population density is achieved, RNA replication and enhanced gene expression is achieved by introduction of the nsp 4 replicase protein into the cells. The protein can be introduced with cationic lipids or, more efficiently, as synthetic fusions with a peptide or protein that has a transport function and allows the fused protein to cross the cell and nuclear membranes (i.e. as Tat, MTS or VP22 fusion proteins).

Therefore, gene expression can be induced at moderate to high levels in the cell population, while retaining viability, by expression of the nsp 1–3 genes and subsequently activation of the 26S promoter. Once cell confluency is reached, replication can be induced by delivery of the nsp 4 replicase protein and cells can be harvested for protein isolation hours later.

Alternatively, the nsp 1–4 proteins can also be delivered to cells. In this case, cells are stably transfected with a vector that encodes the gene of interest under control of the SFV 26S promoter (as in vector 10, 11, or 12 of FIG. 2). Both gene expression and RNA replication are induced by delivery of nsp 1–4 proteins as a complex with cationic lipids or as fusion proteins.

Example 4

Regulation of RNA Replication with MxA Protein

A stable cell line is constructed which expresses the human MxA protein under control of a tetracycline or muristerone-regulated promoter. The expression of the MxA protein is kept in the induced state until RNA replication is required. This stable cell line is then transfected with a vector such as construct 5 of FIG. 1 or a combination of construct 1 (FIG. 1) and construct 10 or 11 (FIG. 2) to express the nsp genes and the gene of interest. RNA replication, however, will be inhibited by the expression of the MxA protein. When MxA expression is shut off either by addition of tetracycline or removal of muristerone from the medium, RNA replication and expression is allowed.

The experimental designs described above are therefore aimed to design a regulated alphavirus expression system, where the gene expression is controlled by controlling the replication of the RNA replicon. The benefit of such a system is to take advantage of the high level expression of the alphavirus systems for recombinant protein production for large scale applications without the biosafety concerns of utilizing a packaged virus.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of controlling alphaviral RNA replication or gene expression in a cell, said method comprising introducing directly into said cell through the cell membrane one or more alphaviral replicase proteins or alphaviral nonstructural proteins.

2. A method for controlling the replication of alphaviral RNA in a cell, said method comprising controlling, with an inducible promoter, the expression of a Mx protein which inhibits or prevents viral RNA replication in said cell.

3. The method of claim 2, wherein said factor is the MxA protein.

4. The method of claim 1, wherein one or more of said replicases or nonstructural proteins are introduced into said cell by using one or more cationic lipids.

5. The method of claim 4, wherein said one or more cationic lipids is lipofectamine or DMRIE-C.

6. The method of claim 1, wherein said one or more replicases or nonstructural proteins are introduced into said cell by fusing said replicases or proteins with a peptide or protein sequence having a transport function such that said replicase protein is transported into said cell.

7. The method of claim 6, wherein said peptide or protein sequence having a transport function is selected from the group consisting of the HIV Tat protein, the Herpesvirus VP22 protein, and membrane translocating sequence (MTS).

8. The method of claim 2, wherein said inducible promoter is a tetracycline-regulated promoter.

9. The method of claim 2, wherein said inducible promoter is a muristerone-regulated promoter.

* * * * *